United States Patent
Govari et al.

(10) Patent No.: US 11,553,961 B2
(45) Date of Patent: Jan. 17, 2023

(54) CATHETER WITH STRETCHABLE IRRIGATION TUBE

(71) Applicant: Biosense Webster (Israel) Ltd., Yokneam (IL)

(72) Inventors: Assaf Govari, Haifa (IL); Christopher Thomas Beeckler, Brea, CA (US); Joseph Thomas Keyes, Sierra Madre, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/863,980

(22) Filed: Apr. 30, 2020

(65) Prior Publication Data

US 2021/0338319 A1    Nov. 4, 2021

(51) Int. Cl.
*A61B 18/14*   (2006.01)
*A61B 18/10*   (2006.01)
*A61B 18/12*   (2006.01)
*A61B 18/00*   (2006.01)

(52) U.S. Cl.
CPC .......... *A61B 18/1492* (2013.01); *A61B 18/10* (2013.01); *A61B 18/1206* (2013.01); *A61B 2018/0022* (2013.01); *A61B 2018/00059* (2013.01); *A61B 2018/00065* (2013.01); *A61B 2018/00267* (2013.01); *A61B 2018/00577* (2013.01); *A61B 2218/002* (2013.01)

(58) Field of Classification Search
CPC ...... A61B 18/1492; A61B 2018/00577; A61B 2018/00059; A61B 2018/00267; A61B 5/6858; A61B 5/6859
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |
| 6,332,089 B1 | 12/2001 | Acker et al. |

(Continued)

FOREIGN PATENT DOCUMENTS

| | | |
|---|---|---|
| WO | WO 1996/005768 A1 | 2/1996 |
| WO | WO 2004/112629 A1 | 12/2004 |

(Continued)

OTHER PUBLICATIONS

European Search Report and Written Opinion dated Oct. 7, 2021, for Application No. 21171209.6, 5 pages.

*Primary Examiner* — Jaymi E Della (74) *Attorney, Agent, or Firm* — Frost Brown Todd LLP (57) ABSTRACT

In one embodiment, a medical system includes a catheter configured to be inserted into a body part of a living subject, and including a deflectable element having a distal end, an expandable distal end assembly disposed at the distal end of the deflectable element, and comprising a plurality of electrodes, a distal portion, and a proximal portion, and configured to expand from a collapsed form to an expanded deployed form, and a stretchable irrigation tube disposed between the distal portion and the proximal portion, and comprising a plurality of irrigation holes, and configured to stretch longitudinally when the distal end assembly is collapsed from the expanded deployed form to the collapsed form.

20 Claims, 7 Drawing Sheets

(56) References Cited

U.S. PATENT DOCUMENTS

| | | |
|---|---|---|
| 6,484,118 B1 | 11/2002 | Govari |
| 6,618,612 B1 | 9/2003 | Acker et al. |
| 6,690,963 B2 | 2/2004 | Ben-Haim et al. |
| 9,474,486 B2 | 10/2016 | Eliason et al. |
| 9,757,180 B2 | 9/2017 | Gelfand et al. |
| 10,362,952 B2 | 7/2019 | Basu et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2007/0083194 A1* | 4/2007 | Kunis ................ A61B 18/1815 606/41 |
| 2009/0171274 A1* | 7/2009 | Harlev .............. A61M 25/0147 604/95.04 |
| 2012/0101413 A1* | 4/2012 | Beetel ................ A61B 18/1492 601/3 |
| 2017/0312012 A1* | 11/2017 | Harlev ................ A61M 25/001 |
| 2018/0014751 A1 | 1/2018 | Hill et al. |
| 2019/0117301 A1 | 4/2019 | Steinke et al. |

FOREIGN PATENT DOCUMENTS

| | | |
|---|---|---|
| WO | WO 2015/187361 A1 | 12/2015 |
| WO | 2019/074733 A1 | 4/2019 |

\* cited by examiner

CATHETER WITH STRETCHABLE IRRIGATION TUBE

FIELD OF THE INVENTION

The present invention relates to medical devices, and in particular, but not exclusively to, catheters.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2020/0065455, issued as U.S. Pat. No. 6,690,963 on Feb. 10, 2004, and 2003/0120150 issued as U.S. Pat. No. 7,729,742 on Jun. 1, 2010, and 2004/0068178, now abandoned. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied through the tip electrode(s) of the ablating catheter, and current flows through the media that surrounds it, i.e., blood and tissue, between the tip electrode(s) and an indifferent electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

US Patent Publication 2019/0117301 of Steinke, et al., issued as U.S. Pat. No. 11,382,688 on Jul. 12, 2022, describes a catheter and catheter system for treatment of a blood vessel of a patient include an elongate flexible catheter body with a radially expandable structure. A plurality of electrodes or other electrosurgical energy delivery surfaces can radially engage material to be treated when the structure expands. A material detector near the distal end of the catheter body may measure circumferential material distribution, and a power source selectively energizes the electrodes to eccentrically treat of a body lumen.

U.S. Pat. No. 9,757,180 to Gelfand, et al., describes systems, devices, and methods for treating a patient having a sympathetically mediated disease associated at least in part with augmented peripheral chemoreflex or heightened sympathetic activation. The treatments include ablating one or more peripheral chemoreceptors or associated afferent nerves to reduce or remove afferent neural signals from the peripheral chemoreceptor.

U.S. Pat. No. 9,474,486 to Eliason, et al., describes an electrophysiology catheter. In one embodiment, the catheter includes an elongated, deformable shaft having a proximal end and a distal end and a basket electrode assembly coupled to the distal end of the shaft. The basket electrode assembly has a proximal end and a distal end and is configured to assume a compressed state and an expanded state. The electrode assembly further includes one or more tubular splines having a plurality of electrodes disposed thereon and a plurality of conductors. Each of the plurality of conductors extends through the tubular spline from a corresponding one of the plurality of electrodes to the proximal end of the basket electrode assembly. The tubular splines are configured to assume a non-planar (e.g., a twisted or helical) shape in the expanded state.

International Patent Publication WO 2019/074733 of St. Jude Medical Cardiology Div. Inc. describes high-density mapping catheters with an array of mapping electrodes. These catheters can be used for diagnosing and treating cardiac arrhythmias, for example. The catheters are adapted to contact tissue and comprise a flexible framework including the electrode array. The array of electrodes may be formed from a plurality of columns of longitudinally-aligned and rows of laterally-aligned electrodes.

U.S. Pat. No. 10,362,952 to Basu, et al., describes a catheter for diagnosing and ablating tissue that has a stabilized spine electrode assembly. The stabilized spine electrode assembly has at least two spines secured to the catheter body at their proximal ends and at least one tether, secured between locations distal of the proximal ends of adjacent spines. The spines have a collapsed arrangement in which the spines are arranged generally along a longitudinal axis of the catheter body and an expanded arrangement in which at least a portion of each spine bows radially outwards from the longitudinal axis and the at least one tether exerts tension on the adjacent spines.

SUMMARY

There is provided in accordance with an embodiment of the present disclosure, a medical system including a catheter configured to be inserted into a body part of a living subject, and including a deflectable element having a distal end, an expandable distal end assembly disposed at the distal end of the deflectable element, and including a plurality of electrodes, a distal portion, and a proximal portion, and configured to expand from a collapsed form to an expanded deployed form, and a stretchable irrigation tube disposed between the distal portion and the proximal portion, and including a plurality of irrigation holes, and configured to stretch longitudinally when the distal end assembly is collapsed from the expanded deployed form to the collapsed form.

Further in accordance with an embodiment of the present disclosure the irrigation holes are disposed radially around the irrigation tube.

Still further in accordance with an embodiment of the present disclosure the irrigation holes are disposed longitudinally along the irrigation tube.

Additionally, in accordance with an embodiment of the present disclosure the irrigation holes are disposed longitudinally along the irrigation tube.

Moreover in accordance with an embodiment of the present disclosure, the system includes an ablation power generator configured to be connected to the catheter, and apply an electrical signal to the electrodes, an irrigation reservoir configured to store irrigation fluid, and a pump configured to be connected to the irrigation reservoir and the catheter, and to pump the irrigation fluid from the irrigation reservoir through the irrigation holes of the irrigation tube.

Further in accordance with an embodiment of the present disclosure a relaxed state of the distal end assembly is the expanded deployed form, the distal end assembly being configured to collapse into the collapsed form when the catheter is retracted in a sheath.

Still further in accordance with an embodiment of the present disclosure a relaxed state of the distal end assembly is the collapsed form, the system further including a puller element disposed inside the deflectable element and the stretchable irrigation tube, and connected to the distal portion of the distal end assembly, and configured when pulled to expand the distal end assembly from the collapsed form to the expanded deployed form.

Additionally, in accordance with an embodiment of the present disclosure the distal end assembly includes a basket assembly.

Moreover, in accordance with an embodiment of the present disclosure the basket assembly includes a plurality of splines.

Further in accordance with an embodiment of the present disclosure the splines include Nitinol.

Still further in accordance with an embodiment of the present disclosure the stretchable irrigation tube includes a biocompatible stretchable material.

Additionally, in accordance with an embodiment of the present disclosure the holes include laser drilled holes.

Moreover, in accordance with an embodiment of the present disclosure the biocompatible stretchable material includes Polyether block amide (PEBA).

Further in accordance with an embodiment of the present disclosure the biocompatible stretchable material is a porous material that includes pores forming at least some of the holes.

Still further in accordance with an embodiment of the present disclosure the biocompatible stretchable material includes expanded Polytetrafluoroethylene (ePTFE).

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Irrigation is commonly used with catheters to provide cooling during medical procedures such as radio-frequency (RF) ablation, for example. One solution for providing irrigation in a basket-type catheter is to have an irrigation channel run through the catheter which terminates in the middle of the basket. Irrigation fluid may then be pumped through the irrigation channel to the distal end of the irrigation channel where the irrigation fluid exits and provides cooling to tissue in the region of the basket as well as diluting blood locally. However, the irrigation is not very well directed and although it may be sufficient for electroporation, which does not generate much heat, it is generally not sufficient to reduce heat created during RF ablation. An additional problem encountered with basket catheters is that the basket needs to be in a collapsed or semi-collapsed form during insertion into the body and then deployed to its expanded form in a body cavity. The requirement to be able to collapse and expand the basket adds further complications to providing effective irrigation as an irrigation channel may interfere with the expansion and collapsing of the basket.

Embodiments of the present invention, provide a catheter with an expandable distal end assembly (such as a basket) including electrodes thereon, with a stretchable irrigation tube fixed between a proximal and distal end of the assembly. The irrigation tube includes holes around the tube to direct irrigation fluid in different directions to provide effective irrigation and cooling. Using a stretchable tube allows the irrigation tube (and therefore the irrigation holes) to extend from the proximal to the distal end of the assembly as the tube stretches and relaxes according to the form of the assembly so that when the assembly is collapsed, the tube is stretched, and when the assembly is expanded, the tube relaxes.

In some embodiments, the holes are disposed along the length of the tube and around the circumference of the tube to provide a much more uniform irrigation spray throughout the distal end assembly. The tube may be made formed from any suitable biocompatible stretchable material, such as Polyether block amide (PEBA) (e.g., PEBAX (with a shore D durometer between 25 and 72)), or a stretchable Polyurethane, a silicone polymer, or expanded Polytetrafluoroethylene (ePTFE). Holes may be made in the tube using any suitable method for example, but not limited to, laser drilling. Some materials such as ePTFE may include pores which are formed when the material is pre-stretched or electrospun. The pores may then provide the irrigation holes in the irrigation tube. When the holes are numerous enough (e.g., with a porous tubes), the irrigation fluid may weep from the tube instead of being sprayed. Nevertheless, providing irrigation via weeping provides sufficient irrigation in many applications.

In some embodiments, the distal end assembly is collapsed by being retracted into a catheter sheath. In other embodiments, the distal end assembly has a naturally collapsed form and pulling a puller wire causes the distal end assembly to expand. The puller wire may be disposed in the stretchable irrigation tube and is connected to the distal end of the distal end assembly.

System Description

Figure 1:
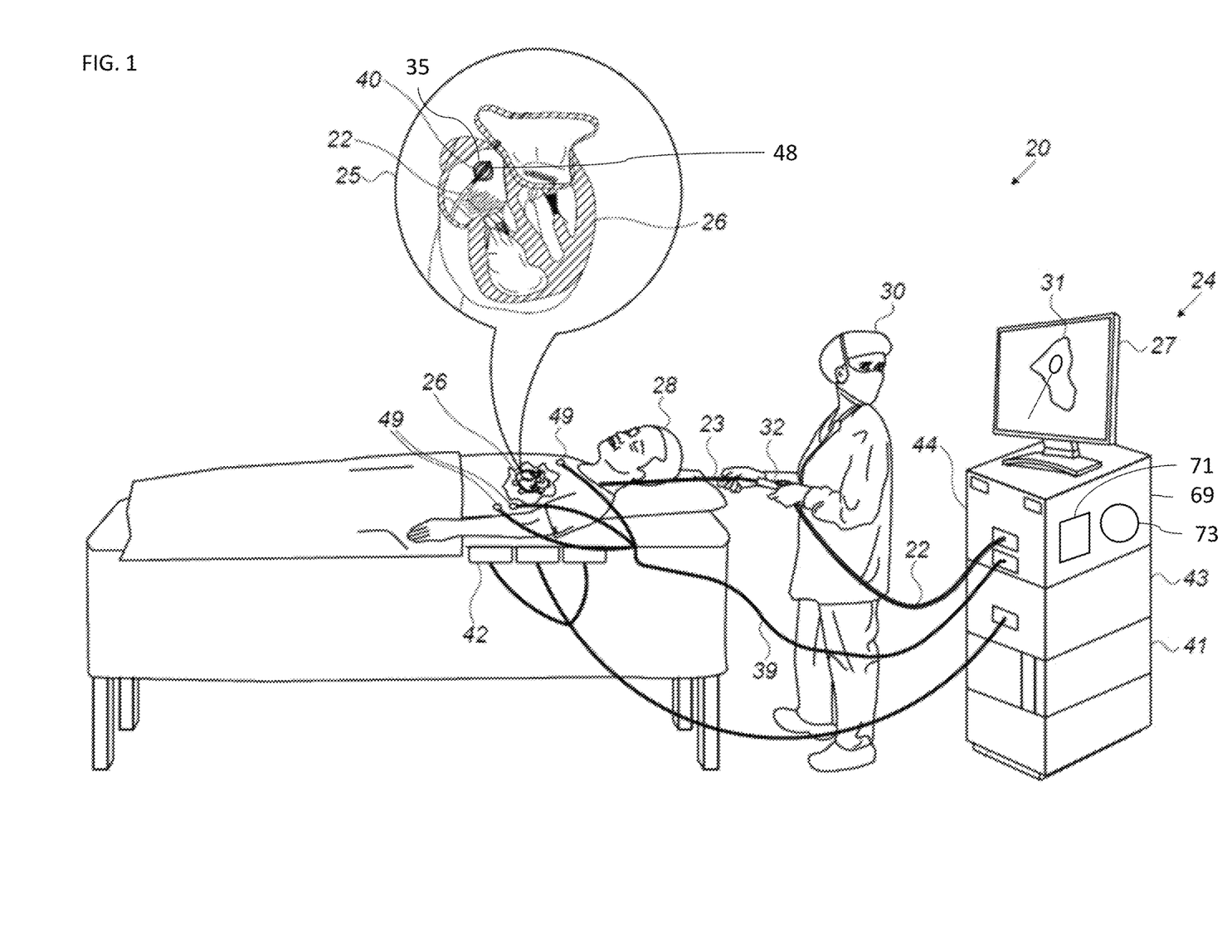
FIG. 1 is a schematic view of a medical system constructed and operative in accordance with an embodiment of the present invention.

Reference is now made to FIG. 1, which is a schematic view of a medical system 20 constructed and operative in accordance with an embodiment of the present invention. The system 20 includes a catheter 40 configured to be inserted into a body part of a living subject (e.g., a patient 28). A physician 30 navigates the catheter 40 (for example, a basket catheter produced Biosense Webster, Inc. of Irvine, Calif., USA), to a target location in a heart 26 of the patient 28, by manipulating an elongated deflectable element 22 of the catheter 40, using a manipulator 32 near a proximal end of the catheter 40, and/or deflection from a sheath 23. In the pictured embodiment, physician 30 uses catheter 40 to perform electro-anatomical mapping of a cardiac chamber and ablation of cardiac tissue.

Catheter 40 includes an expandable distal end assembly 35 (e.g., a basket assembly), which is inserted in a folded configuration, through sheath 23, and only after the catheter 40 exits sheath 23 does the distal end assembly 35 regain its intended functional shape. By containing distal end assembly 35 in a folded configuration, sheath 23 also serves to minimize vascular trauma on its way to the target location.

Catheter 40 includes a plurality of electrodes 48 for sensing electrical activity and/or applying ablation power to ablate tissue of the body part. Catheter 40 may incorporate a magnetic sensor (not shown) at the distal edge of deflectable element 22 (i.e., at the proximal edge of the distal end assembly 35). Typically, although not necessarily, the magnetic sensor is a Single-Axis Sensor (SAS). A second magnetic sensor (not shown) may be included at any suitable position on the assembly 35. The second magnetic sensor may be a Triple-Axis Sensor (TAS) or a Dual-Axis Sensor (DAS), or a SAS by way of example only, based for example on sizing considerations. The magnetic sensors and electrodes 48 disposed on the assembly 35 are connected by wires running through deflectable element 22 to various driver circuitries in a console 24.

In some embodiments, system 20 comprises a magnetic-sensing sub-system to estimate an ellipticity of the basket assembly 35 of catheter 40, as well as its elongation/retraction state, inside a cardiac chamber of heart 26 by estimating the elongation of the basket assembly 35 from the distance between the magnetic sensors. Patient 28 is placed in a magnetic field generated by a pad containing one or more magnetic field generator coils 42, which are driven by a unit 43. The magnetic fields generated by coil(s) 42 transmit alternating magnetic fields into a region where the body-part is located. The transmitted alternating magnetic fields generate signals in the magnetic sensors, which are indicative of position and/or direction. The generated signals are transmitted to console 24 and become corresponding electrical inputs to processing circuitry 41.

The method of position and/or direction sensing using external magnetic fields and magnetic sensors, is implemented in various medical applications, for example, in the CARTO® system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004; 2003/0120150 A1 issued as U.S. Pat. No. 7,729,742 on Jun. 1, 2010, and 2004/0068178 A1, now abandoned.

Processing circuitry 41, typically part of a general-purpose computer, is further connected via a suitable front end and interface circuits 44, to receive signals from body surface-electrodes 49. Processing circuitry 41 is connected to body surface-electrodes 49 by wires running through a cable 39 to the chest of patient 28.

In an embodiment, processing circuitry 41 renders to a display 27, a representation 31 of at least a part of the catheter 40 and a mapped body-part, responsively to computed position coordinates of the catheter 40.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The medical system 20 may also include an ablation power generator 69 (such as an RF signal generator) configured to be connected to the catheter 40, and apply an electrical signal to the electrodes 48. The medical system 20 may also include an irrigation reservoir 71 configured to store irrigation fluid, and a pump 73 configured to be connected to the irrigation reservoir 71 and the catheter 40, and to pump the irrigation fluid from the irrigation reservoir 71 through irrigation holes of an irrigation tube of the catheter 40 as described in more detail with reference to FIGS. 2 and 3.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

Figure 2:
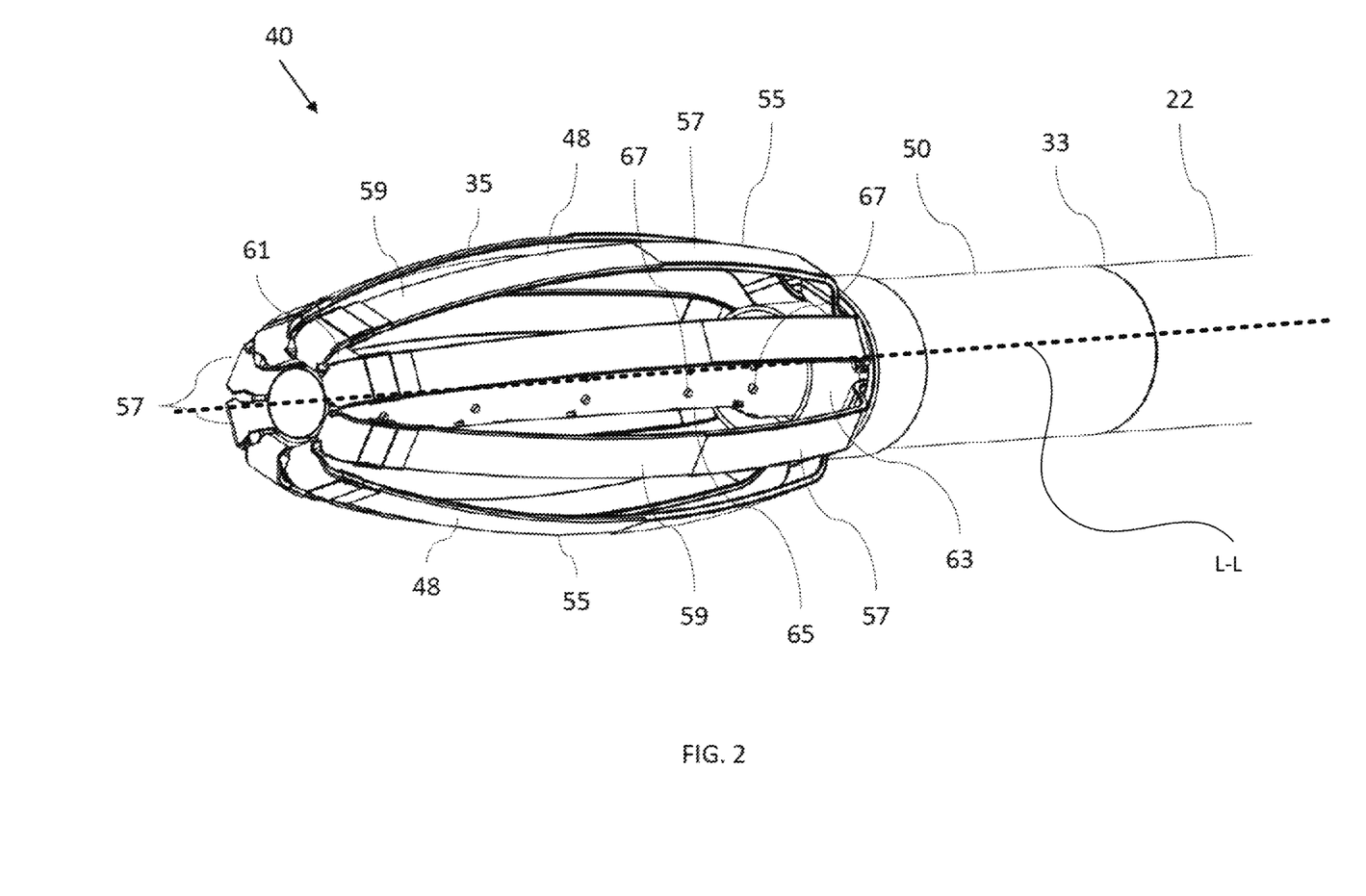
FIG. 2 is a schematic view of a catheter in a collapsed form constructed and operative in accordance with an embodiment of the present invention.
Figure 3:
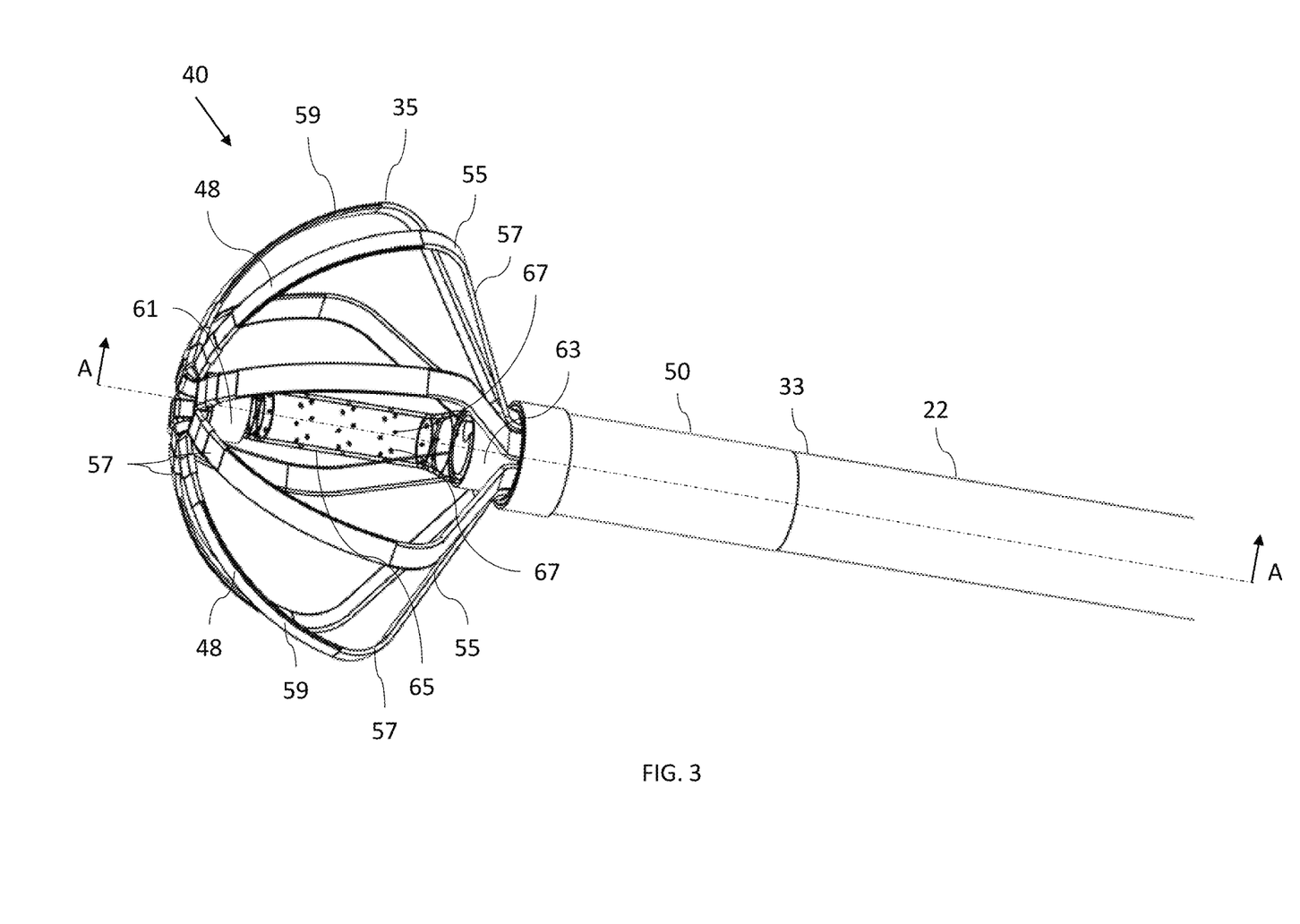
FIG. 3 is a schematic view of the catheter of FIG. 2 in a deployed form.

Reference is now made to FIGS. 2 and 3. FIG. 2 is a schematic view of the catheter 40 in a collapsed form constructed and operative in accordance with an embodiment of the present invention. FIG. 3 is a schematic view of the catheter 40 of FIG. 2 in a deployed expanded form.

The catheter 40 is configured to be inserted into a body part (e.g., the heart 26 (FIG. 1)) of a living subject. The deflectable element 22 of the catheter 40 has a distal end 33. The deflectable element 22 may be produced from any suitable material, for example, polyurethane or polyether block amide. The assembly 35 is disposed distally to the deflectable element 22 and may be connected to the deflectable element 22 via a proximal coupling member 50 at the distal end 33. The proximal coupling member 50 typically comprises a hollow tube and may be formed from any suitable material, for example, but not limited to polycarbonate with or without glass filler, polyether ether ketone (PEEK) with or without glass filler, polyimide, polyamide, or Polyetherimide (PEI) with or without glass filler. The coupling member 50 may formed as an integral part of the deflectable element 22 or as part of the distal end assembly 35 or as a separate element which connects with the deflectable element 22 and the distal end assembly 35.

The assembly 35, which may include a basket assembly, may include multiple splines such as flexible strips 55 (only one labeled for the sake of simplicity). In the embodiments of FIGS. 2 and 3 each flexible strip 55 includes a single electrode 48 (only some labeled for the sake of simplicity). The assembly 35 may include any suitable number of electrodes 48 with multiple electrodes 48 per strip 55.

In the embodiment of FIGS. 2 and 3, each flexible strip 55 is formed of Nitinol which is selectively covered with insulating material in the distal and proximal regions 57 (only some labeled for the sake of simplicity) of the flexible strips 55 leaving a central region 59 (only some labeled for the sake of simplicity) of the flexible strips 55 as an electrically active region to perform mapping and/or perform ablation or electroporation, by way of example. The structure of the assembly 35 may vary. For example, flexible strips 55 (or other splines) may include flexible printed circuit boards (PCBs), or a shape-memory alloy such as Nitinol.

Embodiments described herein refer mainly to a basket distal-end assembly 35, purely by way of example. In alternative embodiments, the disclosed techniques can be used with any other suitable type of distal-end assembly.

The distal end assembly 35 includes a distal portion 61, and a proximal portion 63, and is configured to expand from a collapsed form (shown in FIG. 2) to an expanded deployed form (shown in FIG. 3).

The relaxed state of the distal end assembly 35 is the expanded deployed form shown in FIG. 3. The distal end assembly 35 is configured to collapse into the collapsed form when the catheter 40 is retracted in a sheath 23 (FIG. 1) and is configured to expand to the expanded deployed form when the catheter 40 is removed from the sheath 23. The relaxed shape of the distal end assembly 35 may be set by forming the flexible strips 55 from any suitable resilient material such as Nitinol or PEI.

The catheter 40 includes a stretchable irrigation tube 65 disposed between the distal portion 61 and the proximal portion 63. The stretchable irrigation tube 65 includes a plurality of irrigation holes 67 (only some labeled for the sake of simplicity), and is configured to stretch longitudinally when the distal end assembly 35 is collapsed from the expanded deployed form to the collapsed form. The stretchable irrigation tube 65 includes a biocompatible stretchable material, such as Polyether block amide (PEBA) (e.g., PEBAX (with a shore D durometer between 25 and 72-55D)), or a stretchable Polyurethane, a silicone polymer, or expanded Polytetrafluoroethylene (ePTFE). The stretchable irrigation tube 65 may have any suitable dimensions, for example, an outer diameter in the range of 0.5 mm to 3 mm, e.g., 1.5 mm, a wall thickness in the range of 0.01 mm to 0.5 mm, e.g., 0.125 mm. The holes 67 may have any suitable diameter, for example, in the range of approximately 0.01 mm to approximately 0.2 mm, e.g. approximately 0.165 mm. The tube 65 may include any suitable number of discrete holes, for example, between 1 and 200, e.g. 50. The stretchable irrigation tube 65 is shown in FIG. 3 as a transparent stretchable irrigation tube 65 for the sake of clarity. Alternatively, the stretchable irrigation tube 65 may be translucent or opaque or any suitable combination thereof. The pump 73 (FIG. 1) is configured to pump irrigation fluid from the irrigation reservoir 71 through the irrigation holes 67 of the irrigation tube 65.

In some embodiments, the irrigation holes 67 are disposed radially around the irrigation tube 65 and/or longitudinally along the irrigation tube 65. In other embodiments, the irrigation holes 67 can be disposed such that each hole 67 extends at an angle relative to the longitudinal axis. In one embodiment, each hole may extend at an angle of approximately 90 degrees relative to the longitudinal axis L-L so that the hole is orthogonal with respect to the longitudinal axis L-L. The orientations of the irrigation holes 67 are typically oriented (usually non-parallel to the longitudinal axis L-L) to ensure sufficient coverage of the electrodes with irrigation flow and therefore each irrigation hole 67 may not have the same orientation as its neighbor.

In some embodiments, the holes 67 may include laser or mechanically drilled holes. For example, laser drilled holes may be formed in the biocompatible stretchable material, e.g., in PEBA. In some embodiments, the biocompatible stretchable material, e.g., ePTFE, is a porous material that includes pores forming at least some of the holes 67.

Figure 4:
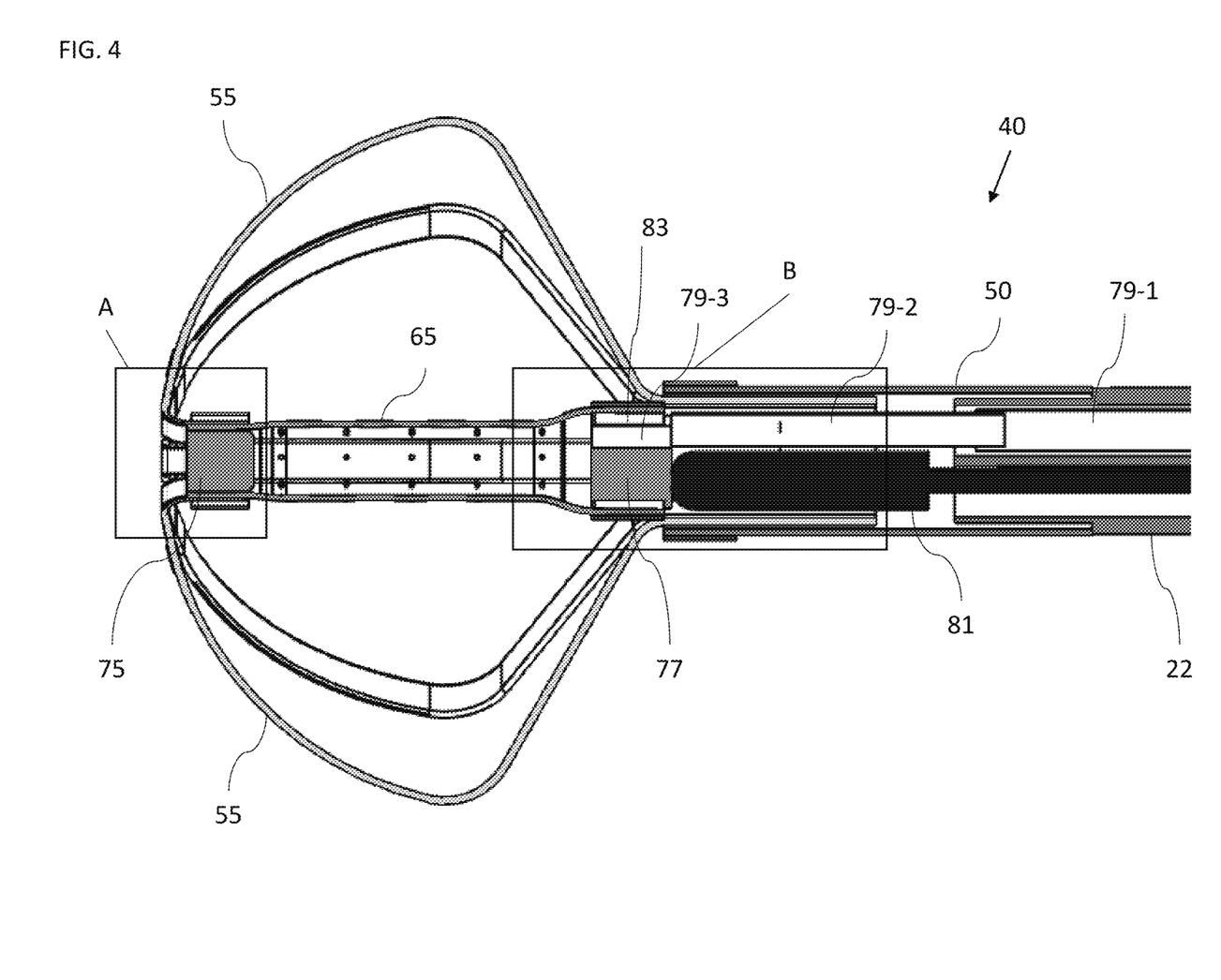
FIG. 4 is a cross-sectional view of the catheter of FIG. 3 along line A:A.

Reference is now made to FIG. 4 is a cross-sectional view of the catheter 40 of FIG. 3 along line A:A. FIG. 4 (inside block A) shows the distal ends of the flexible strips 55 (only two labeled for the sake of simplicity) folded over and connected to a distal connector 75, which in some embodiments is a tube (e.g., polymer tube) or slug (e.g., polymer slug). The distal end of the stretchable irrigation tube 65 is connected to the distal connector 75. The distal connector 75 is described in more detail with reference to FIG. 5.

In some embodiments, the flexible strips 55 may be connected to the distal connector 75 without being folded over so that when the distal end assembly 35 is collapsed the flexible strips 55 are approaching a flat formation along their length.

FIG. 4 (inside block B) shows that the proximal ends of the flexible strips 55 are connected to the proximal coupling member 50. The proximal end of the stretchable irrigation tube 65 is connected to (e.g., stretched over) a proximal connector 77 (for example, a polymer slug). The proximal connector 77 is described in more detail with reference to FIG. 6. FIG. 4 also shows an irrigation line 79 (which extends through the deflectable element 22, the proximal coupling member 50, and a slot 83 in the proximal connector 77) and a position sensor 81 (e.g., a magnetic position sensor).

Figure 5:
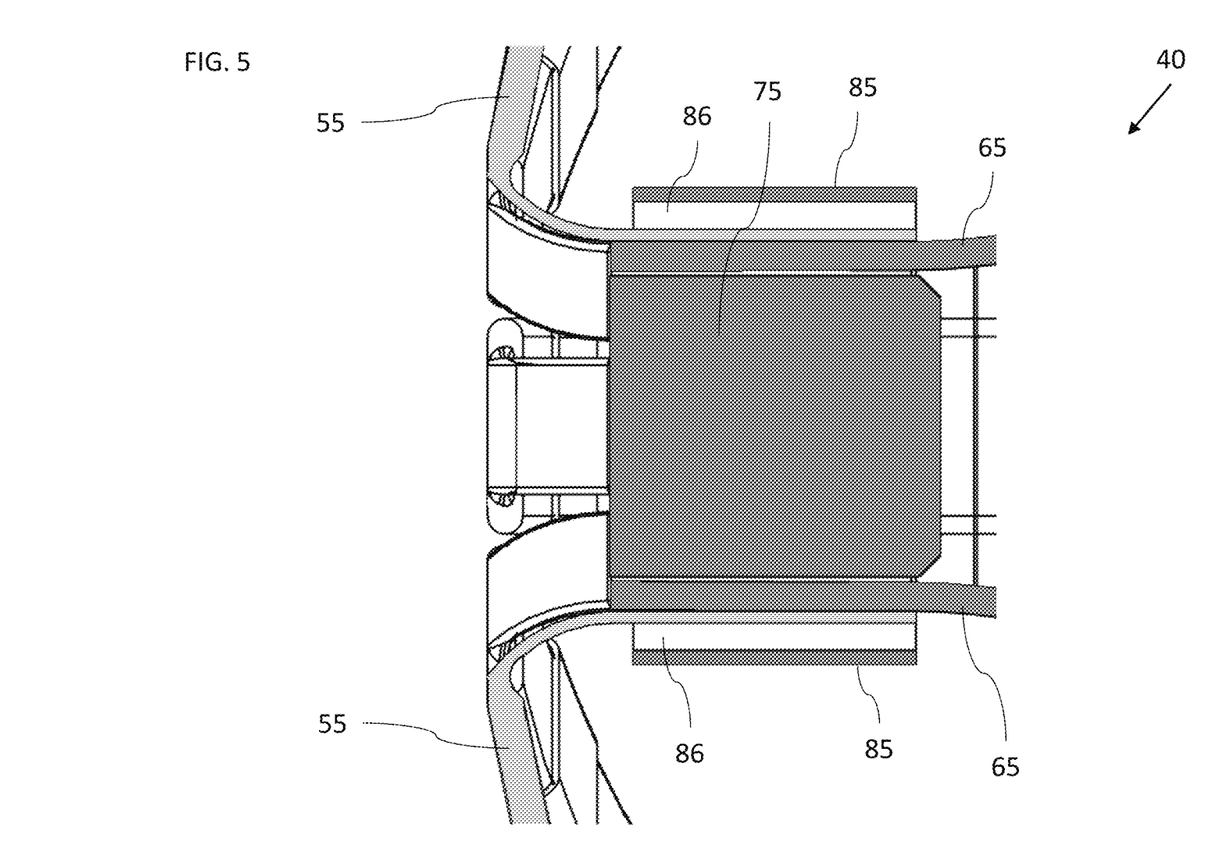
FIG. 5 is a more detailed cross-sectional view of the catheter inside block A of FIG. 4.

Reference is now made to FIG. 5 is a more detailed cross-sectional view of the catheter 40 inside block A of FIG. 4. The distal end of the stretchable irrigation tube 65 is connected to the distal connector 75. The flexible strips 55 are secured between the stretchable irrigation tube 65 and a distal securing ring 85. An adhesive or epoxy layer 86 is disposed between the distal securing ring 85 and the flexible strips 55 thereby securing the securing ring 85 to the flexible strips 55. The stretchable irrigation tube 65 and the flexible strips 55 may be secured using pressure and/or any suitable adhesive. The distal connector 75 and the distal securing ring 85 may be formed from any suitable material, for example, but not limited to polycarbonate with or without glass filler, PEEK with or without glass filler, or PEI with or without glass filler. The distal connector 75 also functions as a slug to plug the distal end of the stretchable irrigation tube 65.

Figure 6:
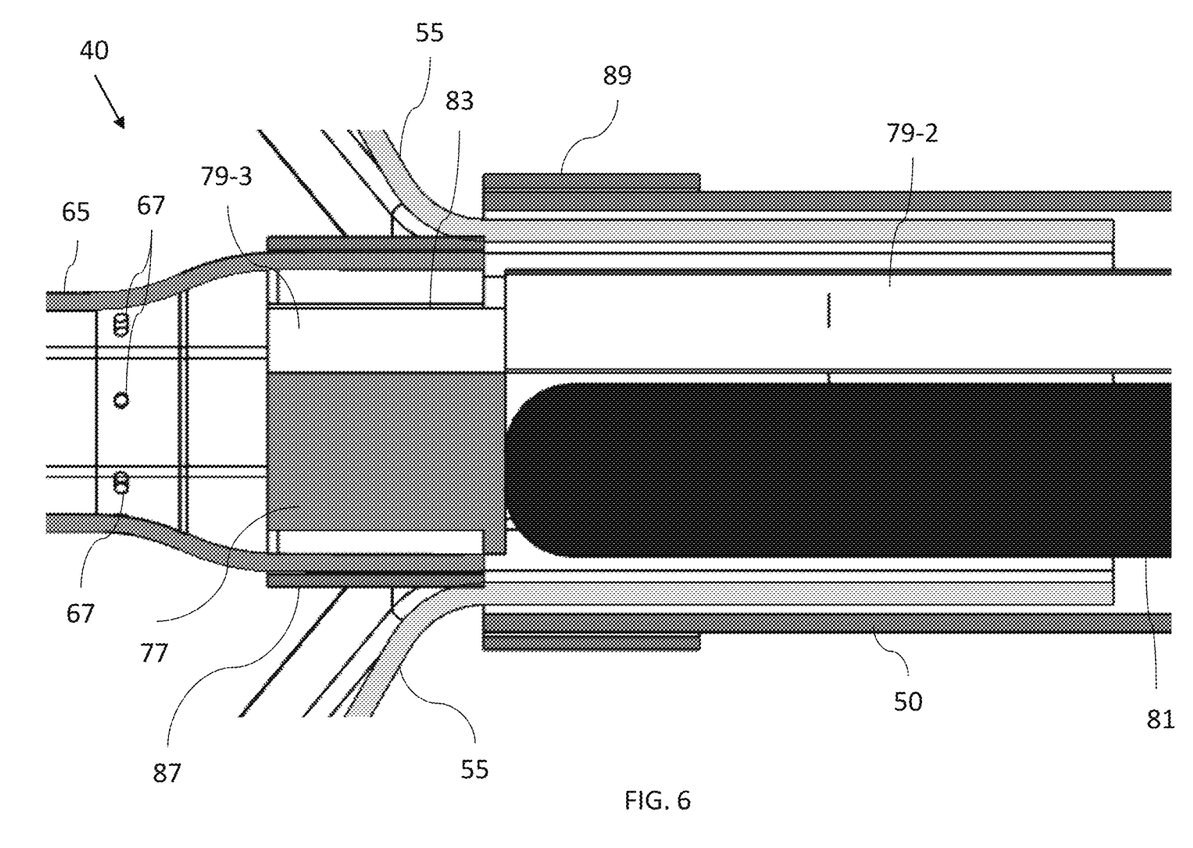
FIG. 6 is a more detailed cross-sectional view of the catheter inside block B of FIG. 4.

Reference is now made to FIG. 6 is a more detailed cross-sectional view of the catheter 40 inside block B of FIG. 4.

FIG. 6 shows the proximal connector 77 with the slot 83. The slot 83 allows the irrigation line 79-3 and electrical wires (e.g., for connection to one or more electrodes and/or sensors) to traverse the proximal connector 77. The irrigation line 79-2 connects to the irrigation line 79-3, which is narrower so that it fits in the slot 83. The stretchable irrigation tube 65 is connected to the proximal connector 77 and is shown as being stretched over the proximal connector 77. The stretchable irrigation tube 65 may be connected to the proximal connector 77 using any suitable connection method. A proximal securing ring 87 is disposed around the stretchable irrigation tube 65 to aid securing the stretchable irrigation tube 65 to the proximal connector 77. The stretchable tube 65 in FIG. 6 is shown partially in an "unstretched" configuration, meaning that the tube 65 is not being elongated along the longitudinal axis L-L (FIG. 7B). Irrigation holes 67 are preferably in the form of a generally circular opening of a diameter of approximately 0.165 mm in the unstretched configuration of tube 65.

The proximal end of the flexible strips 55 are secured between the proximal coupling member 50 and the position sensor 81 and the irrigation line 79-2. Another securing ring 89 is secured over the proximal coupling member 50 to aid securing of the flexible strips 55 to the proximal coupling member 50. The flexible strips 55 may be secured to the proximal coupling member 50 using pressure and/or any suitable adhesive.

The proximal connector 77, the proximal securing ring 87, and the securing ring 89 may be formed from any suitable material, for example, but not limited to polycarbonate with or without glass filler, PEEK with or without glass filler, or PEI with or without glass filler.

Figure 7A:
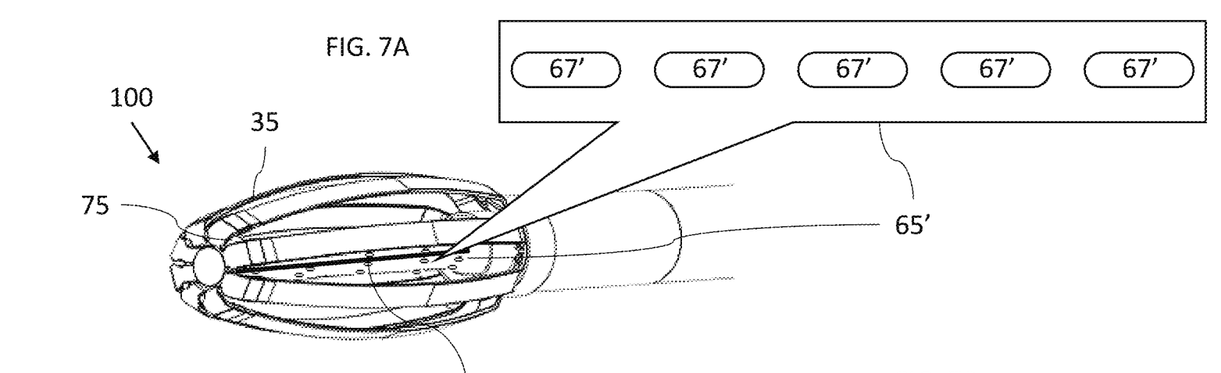
FIG. 7A is a schematic view of a catheter in a collapsed form constructed and operative in accordance with an alternative embodiment of the present invention.
Figure 7B:
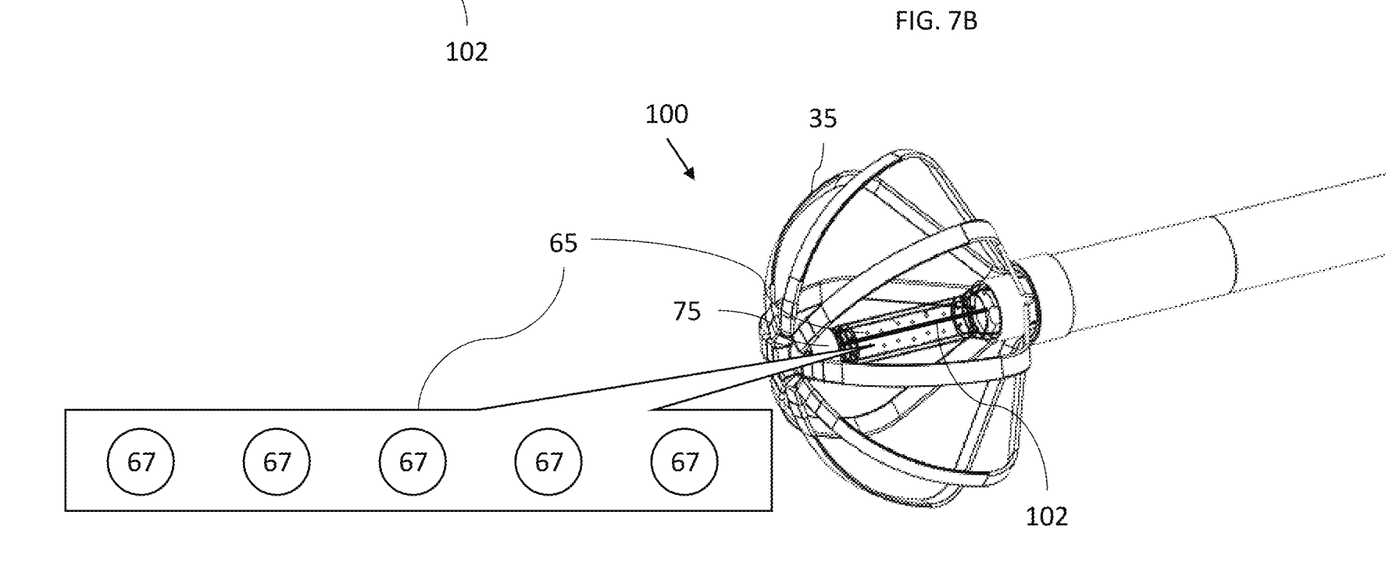
FIG. 7B is a schematic view of the catheter of FIG. 7A in a deployed form.

Reference is now made to FIGS. 7A and 7B. FIG. 7A is a schematic view of a catheter 100 in a collapsed form constructed and operative in accordance with an alternative embodiment of the present invention. FIG. 7B is a schematic view of the catheter 100 of FIG. 7A in a deployed and expanded form having a larger outer profile than the collapsed form of catheter 100. In the collapsed configuration of the basket catheter 100, tube 65 is in a "stretched" configuration (designated as elongated tube 65') that elongates tube by about 80% of the original unstretched length of tube 65 to arrive at the elongated tube 65' being longer than the unstretched length of tube 65. In this configuration, it can be seen in the inset of FIG. 7A of the elongated tube 65' causes the circular irrigation holes 67 (of FIG. 6) to take on a slot like (i.e., rounded rectangular) perimeter 67' of approximately 0.15 mm by 0.5 mm (e.g., opening 67' is approximately 250% increase in area of the original opening 67) due to the elongation of tube 65'. In the expanded configuration of basket 100 shown in FIG. 7B, the tube 65 is not being stretched along longitudinal axis L-L as shown by the inset schematic representation of tube 65. In the unstretched tube configuration 65 for FIG. 7B, the irrigation holes 65 approximates a circular opening to allow irrigation fluid to flow through. In one embodiment, the unstretched length of tube 65 is approximately 6 mm and the elongated length 65' (of the original tube 65) is approximately 11 mm.

The catheter 100 is substantially the same as the catheter 40 of FIGS. 1-6 apart from the following differences. The relaxed state of the distal end assembly 35 of the catheter 100 is the collapsed form of the distal end assembly 35 shown in FIG. 7A, which relaxed state of the basket 100 causes the stretching or elongation of the stretchable tube 65'. The relaxed state may be configured by using a resilient material, for example, PEI or a shape-memory alloy such as Nitinol.

The catheter 100 includes a puller element 102 (e.g., a puller wire) disposed inside the deflectable element 22 and the stretchable irrigation tube 65, and connected to the distal portion 61 of the distal end assembly 35. The puller element 102 may be formed from any suitable material, for example, stainless steel, nitinol, and/or ultra-high-molecular-weight polyethylene (UHMWPE). The puller element 102 may have any suitable outer diameter, for example, in the range of 0.05 mm to 0.5 mm, e.g., 0.175 mm. In some embodiments the puller element 102 is connected to the distal connector 75. The puller element 102 is configured when pulled to expand the distal end assembly 35 from the collapsed form (shown in FIG. 7A) to the expanded deployed form (shown in FIG. 7B). The puller element 102 may be connected to the manipulator 32 (FIG. 1), which controls the puller element 102 to deploy the assembly 35 and change an ellipticity of the assembly 35 according to the longitudinal displacement of the puller element 102 with respect to the deflectable element 22.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A medical system comprising a catheter configured to be inserted into a body part of a living subject, and including:
   (a) a deflectable element having a distal end;
   (b) an expandable distal end assembly disposed at the distal end of the deflectable element, and comprising:
      (i) a plurality of electrodes,
      (ii) a distal portion, and
      (iii) a proximal portion, the distal end assembly being configured to expand from a collapsed form to an expanded deployed form; and
   (c) a stretchable irrigation tube disposed between the distal portion and the proximal portion, and comprising:
      (i) a distal tube end fixedly coupled to the distal portion of the distal end assembly, and (ii) a plurality of irrigation holes, the stretchable irrigation tube configured to stretch longitudinally when the distal end assembly is collapsed from the expanded deployed form to the collapsed form.

2. The system according to claim 1, the irrigation holes being disposed radially around the irrigation tube.

3. The system according to claim 2, the irrigation holes being disposed longitudinally along the irrigation tube.

4. The system according to claim 1, the plurality of irrigation holes being disposed longitudinally along the irrigation tube.

5. The system according to claim 1, further comprising:
(a) an ablation power generator configured to be connected to the catheter, and apply an electrical signal to the plurality of electrodes;
(b) an irrigation reservoir configured to store irrigation fluid; and
(c) a pump configured to be connected to the irrigation reservoir and the catheter, and to pump the irrigation fluid from the irrigation reservoir through the plurality of irrigation holes of the irrigation tube.

6. The system according to claim 1, a relaxed state of the distal end assembly being the expanded deployed form, the distal end assembly being configured to collapse into the collapsed form when the catheter is retracted in a sheath.

7. The system according to claim 1, a relaxed state of the distal end assembly being the collapsed form, the system further comprising a puller element disposed inside the deflectable element and the stretchable irrigation tube, and connected to the distal portion of the distal end assembly, and configured when pulled to expand the distal end assembly from the collapsed form to the expanded deployed form.

8. The system according to claim 1, the distal end assembly including a basket assembly.

9. The system according to claim 8, the basket assembly including a plurality of splines.

10. The system according to claim 9, the plurality of splines including Nitinol.

11. The system according to claim 1, the stretchable irrigation tube including a biocompatible stretchable material.

12. The system according to claim 11, the plurality of irrigation holes including laser drilled holes.

13. The system according to claim 11, the biocompatible stretchable material including Polyether block amide (PEBA).

14. The system according to claim 11, the biocompatible stretchable material comprising a porous material that includes pores forming at least some of the plurality of irrigation holes.

15. The system according to claim 14, the biocompatible stretchable material including expanded Polytetrafluoroethylene (ePTFE).

16. A catheter device comprising:
(a) a deflectable element having a distal end;
(b) an expandable distal end assembly disposed at the distal end of the deflectable element, and comprising:
(i) a plurality of electrodes, and
(ii) a distal portion extending along a longitudinal axis to a proximal portion, the distal end assembly being configured to expand from a collapsed form to an expanded deployed form; and
(c) a stretchable irrigation tube disposed between the distal portion and the proximal portion along the longitudinal axis, and comprising:
(i) a distal tube end fixedly coupled to the distal portion of the distal end assembly, and
(ii) a plurality of irrigation holes extending through the tube in a direction non-parallel to the longitudinal axis, the stretchable irrigation tube configured to stretch to an elongated length along the longitudinal axis when the distal end assembly is collapsed.

17. The catheter device of claim 16, each of the plurality of irrigation holes defining a circular perimeter when the stretchable irrigation tube is in a first configuration having an unstretched length shorter than the elongated length.

18. The catheter device of claim 16, each of the plurality of irrigation holes defining a rounded rectangular perimeter when the stretchable irrigation tube is stretched to the elongated length.

19. The catheter device of claim 16, the elongated length comprising any length from approximately 20% to approximately 80% greater length than an unstretched length of the stretchable irrigation tube.

20. The catheter of claim 16, the plurality of irrigation holes extending generally orthogonal to the longitudinal axis.

* * * * *

UNITED STATES PATENT AND TRADEMARK OFFICE
CERTIFICATE OF CORRECTION

PATENT NO. : 11,553,961 B2
APPLICATION NO. : 16/863980
DATED : January 17, 2023
INVENTOR(S) : Assaf Govari et al.

Page 1 of 1

It is certified that error appears in the above-identified patent and that said Letters Patent is hereby corrected as shown below:

In the Specification

Column 1, Line 25, recites:
Nos. 2020/0065455, issued as U.S. Pat. No. 6,690,963 on
Should read:
Nos. 2002/0065455, issued as U.S. Pat. No. 6,690,963 on Signed and Sealed this
Twenty-seventh Day of February, 2024

Katherine Kelly Vidal
*Director of the United States Patent and Trademark Office*